United States Patent [19]

Bozon et al.

[11] 4,362,605

[45] Dec. 7, 1982

[54] SENSOR FOR MEASURING THE OXYGEN CONTENT IN THE EXHAUST GAS OF COMBUSTION ENGINES AND METHOD THEREOF

[75] Inventors: Alfred Bozon, Erlensee; Edgar Koberstein, Alzenau; Hans-Dieter Pletka, Freigericht; Herbert Voelker, Hanau, all of Fed. Rep. of Germany

[73] Assignee: Degussa Aktiengesellschaft, Frankfurt, Fed. Rep. of Germany

[21] Appl. No.: 183,774

[22] Filed: Sep. 3, 1980

[30] Foreign Application Priority Data

Sep. 19, 1979 [DE] Fed. Rep. of Germany ....... 2937802

[51] Int. Cl.$^3$ ............................................. G01N 27/58
[52] U.S. Cl. .................................... 204/1 T; 60/276; 123/489; 204/195 S
[58] Field of Search .............. 204/1 S, 195 S; 60/276; 123/489

[56] References Cited

U.S. PATENT DOCUMENTS

| | | | |
|---|---|---|---|
| 3,935,089 | 1/1976 | Togawa et al. | 204/195 S |
| 3,981,785 | 9/1976 | Sandler | 204/195 S |
| 4,132,615 | 1/1979 | Linder et al. | 204/195 S |
| 4,199,425 | 4/1980 | Sinkevitch | 204/195 S |
| 4,240,890 | 12/1980 | Watanabe et al. | 204/195 S |
| 4,253,302 | 3/1981 | Asano et al. | 60/276 |

Primary Examiner—G. L. Kaplan
Attorney, Agent, or Firm—Beveridge, DeGrandi & Kline

[57] ABSTRACT

An improved lambda sensor is disclosed for the measurement of the oxygen content in the exhaust gas of internal combustion engines in which the sensor element is provided with a gas permeable wrapping coated with a catalyst. The sensor delivers a clear well defined signal in the so-called rich exhaust gas, which makes possible a more precise adjustment of the fuel-air mixture fed to the internal combustion engine.

6 Claims, 14 Drawing Figures

FIG.1

λ-PROBE SIGNAL BEFORE AND AFTER CATALYST

SENSOR FOR MEASURING THE OXYGEN CONTENT IN THE EXHAUST GAS OF COMBUSTION ENGINES AND METHOD THEREOF

The invention relates to an improved sensor for measuring the oxygen content in the exhaust gas of internal combustion engines which will permit even in the rich exhaust gas range ($\lambda \leq 1$) to obtain a probe signal sufficiently well defined for a favorable adjustment of the mixture.

BACKGROUND OF THE INVENTION

For the decontamination of exhaust gases from internal combustion engines, in addition to the oxidation catalysts also multifunctional catalysts, so-called three-way catalysts, are being used more and more. These three-way catalyst have the characteristic of simultaneously converting the harmful substances of CO, HC and $NO_X$ in a certain area of the exhaust gas composition. In order to maintain this area of the exhaust gas composition, the catalysts in motor vehicles are used in combination with a controllable carburetor or an injection device ("closed loop") for the cleaning of the exhaust gas. At the same time, the $O_2$ content of the exhaust gas is determined by means of an oxygen sensor, the so-called $\lambda$ (lambda) - sensor. The sensor produces a voltage up to 800 mV, corresponding to the $O_2$ partial pressure prevailing in the exhaust gas. This voltage is electronically amplified and controls via a regulator the formation of the mixture of the injection system or of a carburetor. The control should take place in such a way that the composition of the exhaust gas mixture always makes possible the optimum and simultaneous conversion of CO, HC and $NO_X$ in as narrow band width as possible at the most favorable point of operation of the catalyst.

The mean operating range of currently used three-way catalysts lies at $\lambda = 0.985 - 1.00$; that is to say, barely in the rich area of the air/fuel mixture. The oxygen sensor consequently is admitted with rich exhaust gas. As has been found, the sensor signal, which is measured before the catalyst, is adulterated by the hydrogen and CO components contained in the exhaust gas. This sensor signal is then not well defined. As a result of this, the sensor voltage exceeds the control range of the system which leads to an overshooting of the mixture formation and thus to an increase of the emissions. Especially in the case of converting the nitric oxides however a precise adjustment of the formation of the mixture has a favorable effect on the optimum operation point of a three-way catalyst.

SUMMARY OF THE INVENTION

It is the task of the invention to improve an oxygen measuring sensor located in a rich flow of exhaust gas in such a way that ill defined probe signals will be avoided and thus overshootings of the formation of the mixture will be prevented.

It was now found surprisingly that by wrapping the sensor element of an oxygen sensor placed in a rich flow of exhaust gas, with a catalytically active, gas permeable wrapping, a clear well defined sensor signal eminently suitable for the adjustment of the mixture, will be obtained. It is an object of the invention to provide an improved sensor for the measuring of the oxygen content in the exhaust gas of internal combustion engines, which is characterized by the fact that the measuring of solid state electrolyte, sensor element, serving as a producer of the electric sensor signal and being in the stream of exhaust gas, is provided with a catalytically active, gas permeable, wrapping spaced apart and not touching said sensor element.

DETAILED DESCRIPTION OF THE INVENTION

According to a preferred development of the invention, the sensor element itself or a sensor surrounded by a perforated, protective tube is wrapped in one or more layers with a wire gauze of heat resistant steel free of scale, impregnated or coated with a catalyst material.

The catalyst material may be deposited directly on the wrapping or on a catalysis promoting metal oxide intermediate layer which, itself, is applied to the wrapping. A particularly favorable variation of the invention uses a catalysis promoting intermediate layer of an aluminum oxide of the transition series. This aluminum oxide may also contain additions of oxides of the elements cerium, zinconium, iron, nickel, tin, zinc, molybdenum, the rare earths, as well as calcium, strontium and barium or mixtures thereof. By aluminum oxide of the transition series, it is to be understood to mean an active aluminum oxide promoting catalysis, which may contain the following crystallographically determinable phases: $\gamma$-, $\delta$-, $\eta$-, $\theta$ or $\chi$ and $\chi$-$Al_2O_3$.

According to the invention, the improvement of commercial oxygen sensors points out a simple and cheap way how the control system for the air/fuel mixture of internal combustion engines may be considerably improved with reference to its control behavior. With a precise control system, beside saving of fuel, above all essentially improved emission values will be achieved since the optimal operating point of a three-way catalyst used in the system may be maintained more precisely. Especially, the nitric oxide conversion is drastically improved.

An additional advantage lies in the fact that the wrapping coated with aluminum oxide or some other highly surface active substance simultaneously acts as a filter and protects the sensor element of the lambda sensor against the deposits which originate from fuel and oil additives. This, under certain circumstances, may bring about an extension of the useful life of now 15,000 miles to longer times.

The catalyst material may consist of metals of the platinum group, optionally in combination with non-noble metals, such as aluminum or nickel. Suitable metals of the platinum group include platinum, ruthenium, palladium, iridium and rhodium, mixtures or alloys of these mixtures, for example, platinum/palladium, platinum/rhodium, platinum/palladium/rhodium, platinum/iridium, platinum/palladium/iridium. Preferred are platinum/rhodium compositions or platinum/rhodium/aluminum compositions. Whenever a multiplicity of catalyst metals is used, they may be deposited separately or simultaneously on the carrier. For economic reasons, the portion of platinum group metals as a catalytically active element in the probe wrapping should not exceed 15% by weight and may amount to 0.01–12% by weight, preferably to 1–10% by weight.

Whenever the platinum group component of the wrapping contains more than one of these metals, said component may be present in a weight ratio between platinum and the remaining platinum group metals between 1:3 to 20:1. The portion of one or several non-noble metals may amount altogether to a multiple of the platinum group metal content.

The application of the catalytically active component the wire gauze may, according to one of the pertinent and known methods, be accomplished for example by impregnation. There also is the possibility of depositing the noble metal galvanically by electroplating or by vacuum metallizing, on the surface of the metal.

As a material for the wrapping of the probe, for example, a wire gauze made of a heat resistant, aluminum containing stainless steel alloy free of scale, has been found to be suitable. Such working materials consist for example of iron chromium, aluminum, as well as possibly of cerium or yttrium containing alloys. Working material No. 1,4725 according to DIN is such a material. However, alloys like Kanthal D, rustproof steel 316 Inconel 600, 601 and other alloys, for example, listed in the German OS No. 24 50 664, may be used and the disclosure thereof is incorporated herein.

The wire gauze may have a mesh width of 0.2–0.025, preferably 0.15–0.05, especially 0.1 mm and a wire gauge of 0.15–0.025, preferably 0.1–0.05, and especially 0.07 mm.

A further feature of the invention resides in the use of the improved sensor for the production of a voltage corresponding to the residual oxygen concentration in the exhaust gases of internal combustion engines, as a value for the adjustment of the combustion of the air/fuel ratio.

The invention will be explained in more detail in connection with the drawing and subsequently on the basis of embodiments given by way of example.

Figure 1:
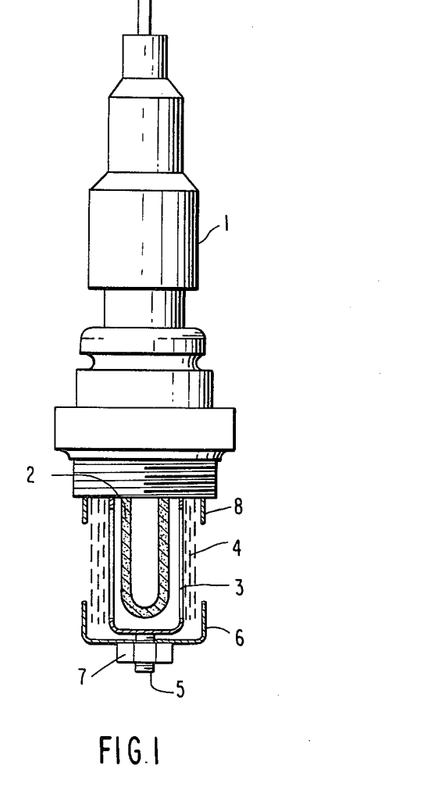
FIG. 1 is a schematic view of an improved oxygen sensor according to the invention.

According to FIG. 1, a $\lambda$-sensor such as manufactured by the firm Robert Bosch GmbH, Stuttgart, as illustrated on page 9 of the article by Grunde T. Engh and Stephen Wallmann, published in Society of Automotive Engineers, 400 Commonwealth Dr., Warrendale, Pa. 15096, USA—No. 770295, is utilized and modified in accordance with one embodiment of the invention.

A sensor body 1 which is screwed in the manner of a spark plug into a threaded opening in the exhaust gas channel, is provided at its lower end with a zirconium dioxide sensor element 2 coated on its inside and outside with a platinum and spinel protective layer developed as a solid state electrolyte body, which is enclosed by a cylindrical protective jacket of heat resistant metal 3. The longitudinal side of the jacket is slit, the headside or end of the jacket consists of solid material. The rear part of the protective jacket is fitted in between the detector and that part of the body of the probe carrying the thread. Fitting against the longitudinal part of the protective jacket, three superimposed layers of a wire gauze 4 of working material No. 1,4725 according to DIN with an outside surface of about $3 \times 6$ cm$^2$ are wound up one on top of the other.

The wire gauze consists of wires with a diameter of 0.07 mm and a mesh width of 0.1 mm and is coated with a catalyst material.

In the solid material of the protective jacket at the head of the probe in the center, a threaded pin 5 is attached. Above it a centrally drilled cap 6 made of scale resistant and heat resistant metal is positioned which embraces the layers 4 of the wire gauze at their lower end. The cap is being screwed onto the head of the sensor with a secured nut 7. Following the "spark plug thread" of the probe body 1, a retainer ring 8 encircling the upper end of the screen cloth layers 4 is attached.

It is obvious that other sensors which are on the market may be modified in a similar manner, whereby as an attaching means for the catalyst carrier, clamping, welding or soldering may also be made use of. Also, a fixed screen cloth cap may be attached to the base of the thread of the probe body. Instead of a metallic screen cloth carrier 4, some gas permeable ceramics, thus for example, highly porous solid ceramics, or a gas permeable ceramic network may be used, which is attached to the probe body 1 either by mechanical means or by cementing on with a temperature resistant cement.

Figures 2, 2A:
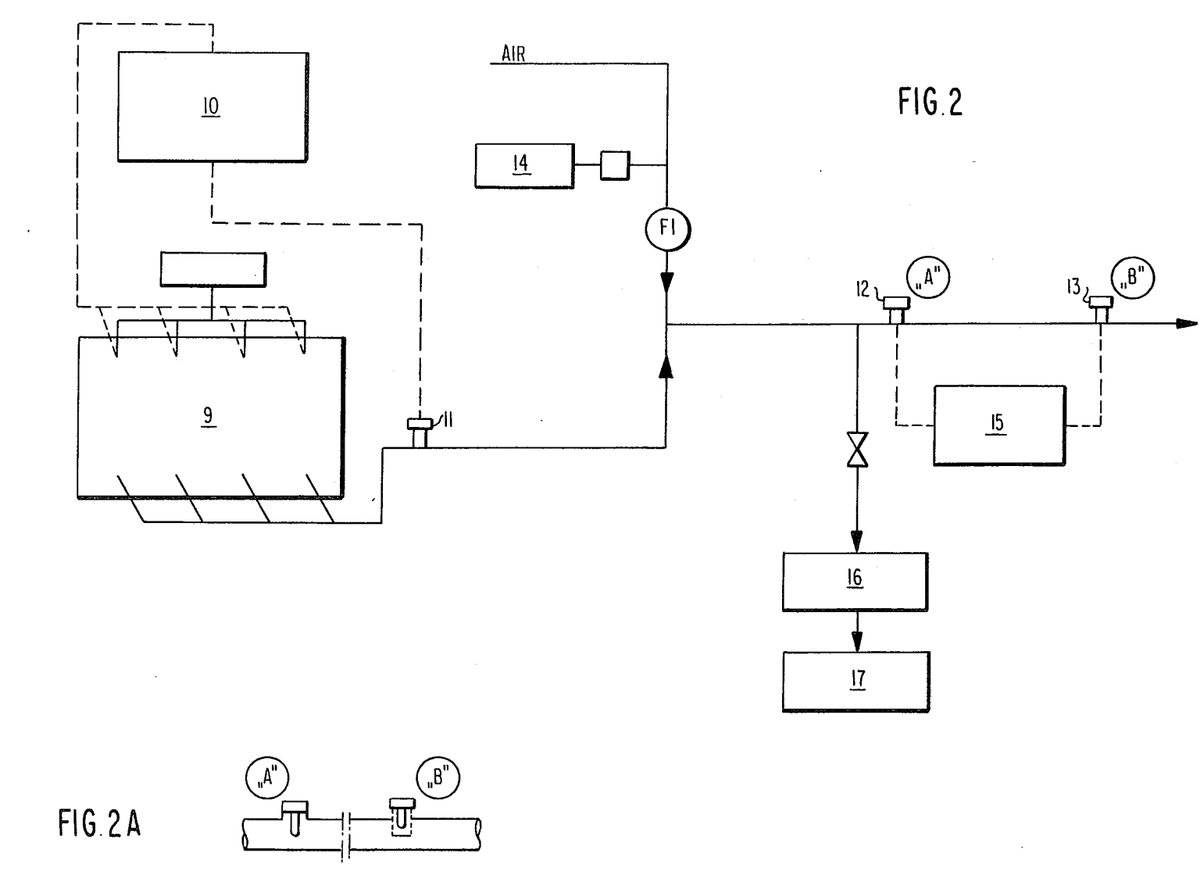
FIG. 2 is a schematic diagram showing the arrangement used for testing the $\lambda$-sensor according to the invention from the point of view of application technology.
FIG. 2A shows additional details of the sensors of FIG. 2.
Figure 3:
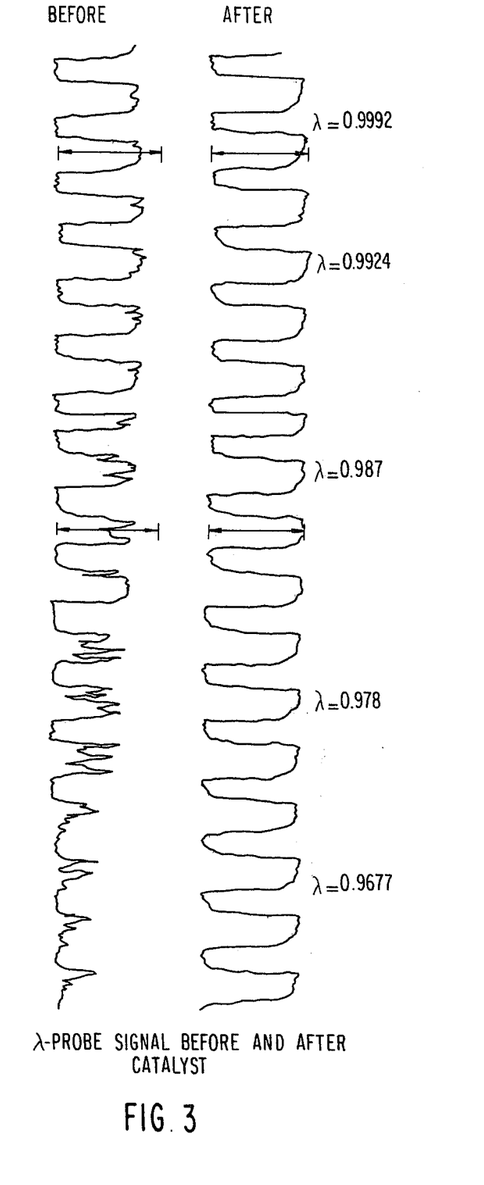
FIG. 3 is a diagram showing the oxygen-sensor signal before and after an auto exhaust gas cleaning catalyst in the case of rich air/fuel conditions of $\lambda = 0.9677–0.9992$.
Figure 4A:
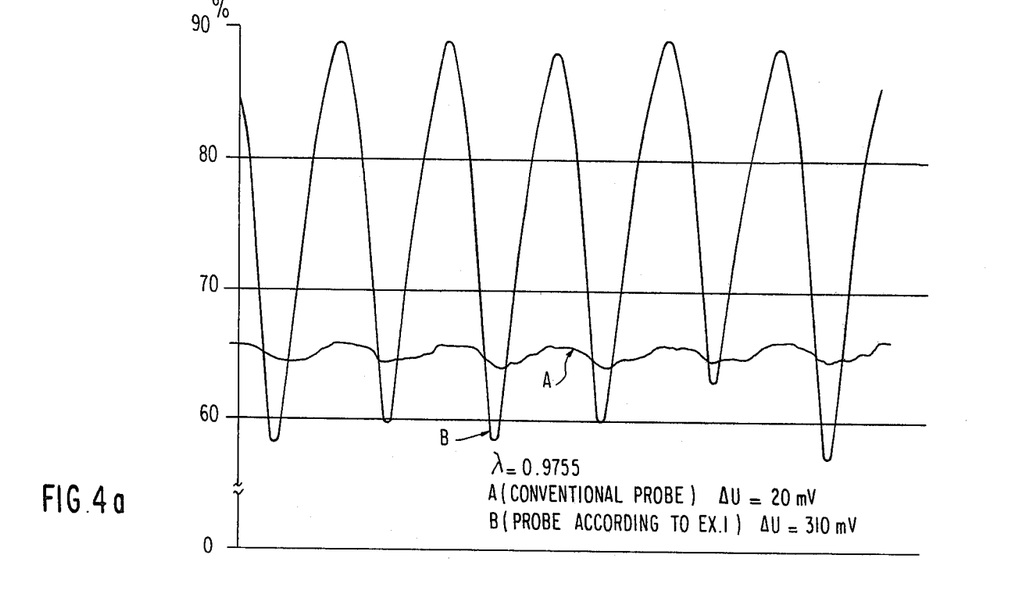
FIGS. 4a–4e are graphs showing sensor signals of a commerical oxygen sensor and of an oxygen sensor according to the invention, in the case of air/fuel ratios of $\lambda = 0.9755–1.0231$, wherein the platinum group metal component was applied directly onto the probe wrapping after 30 hours of annealing it at 900° C. in air.
Figure 4B:
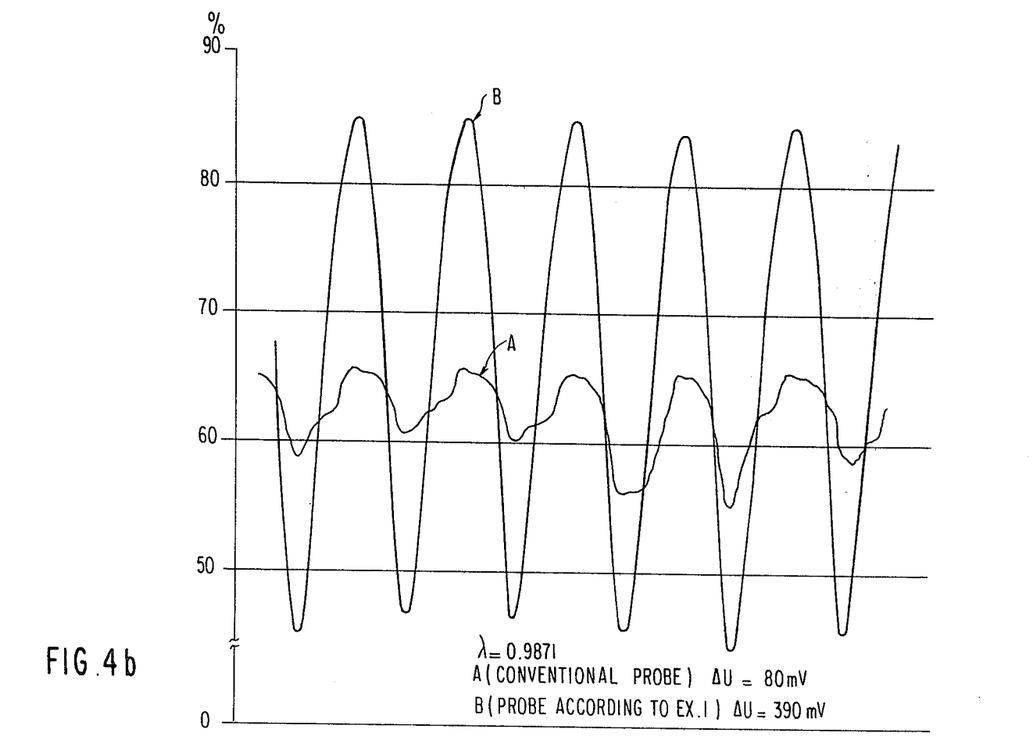
Figure 4C:
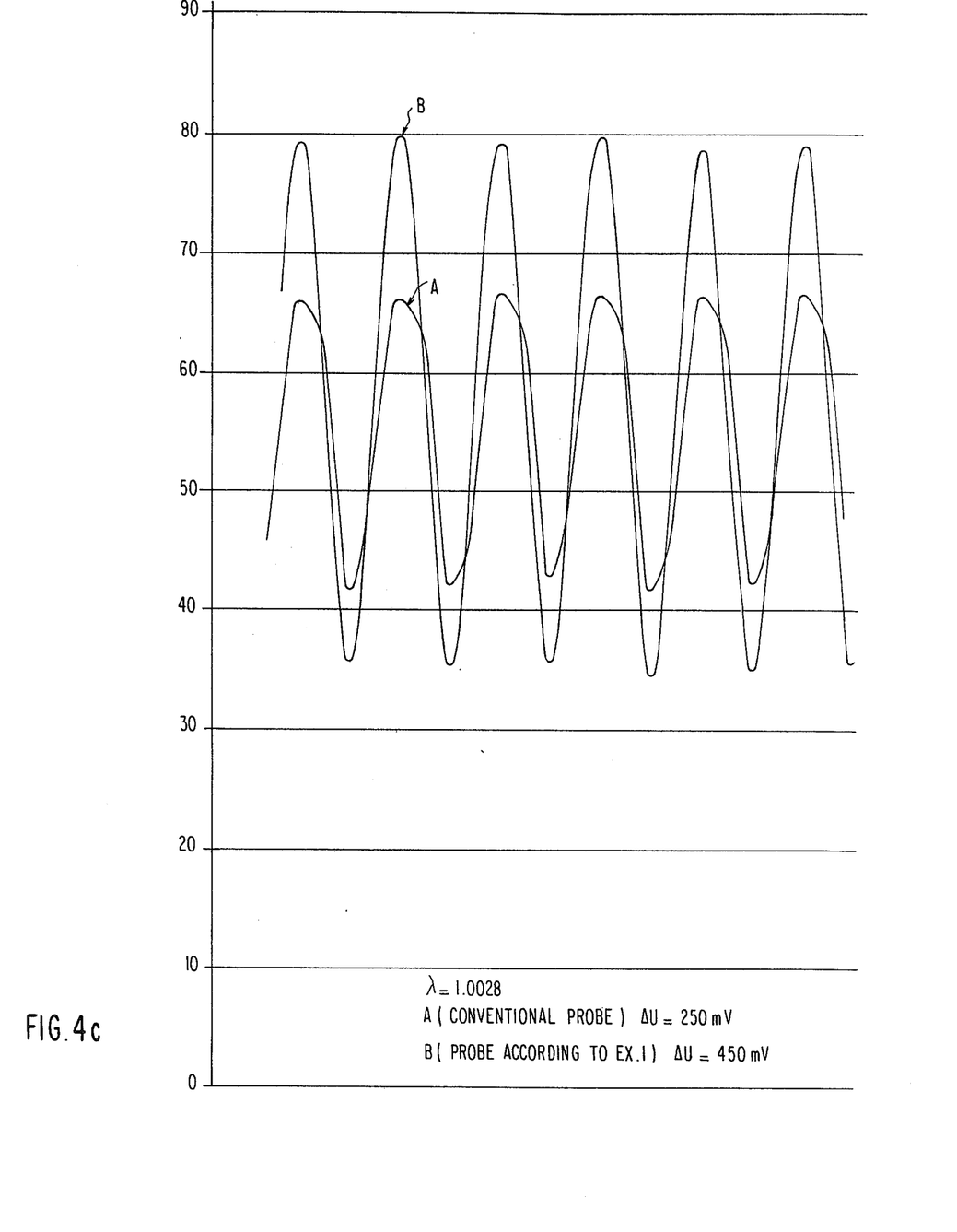
Figure 4D:
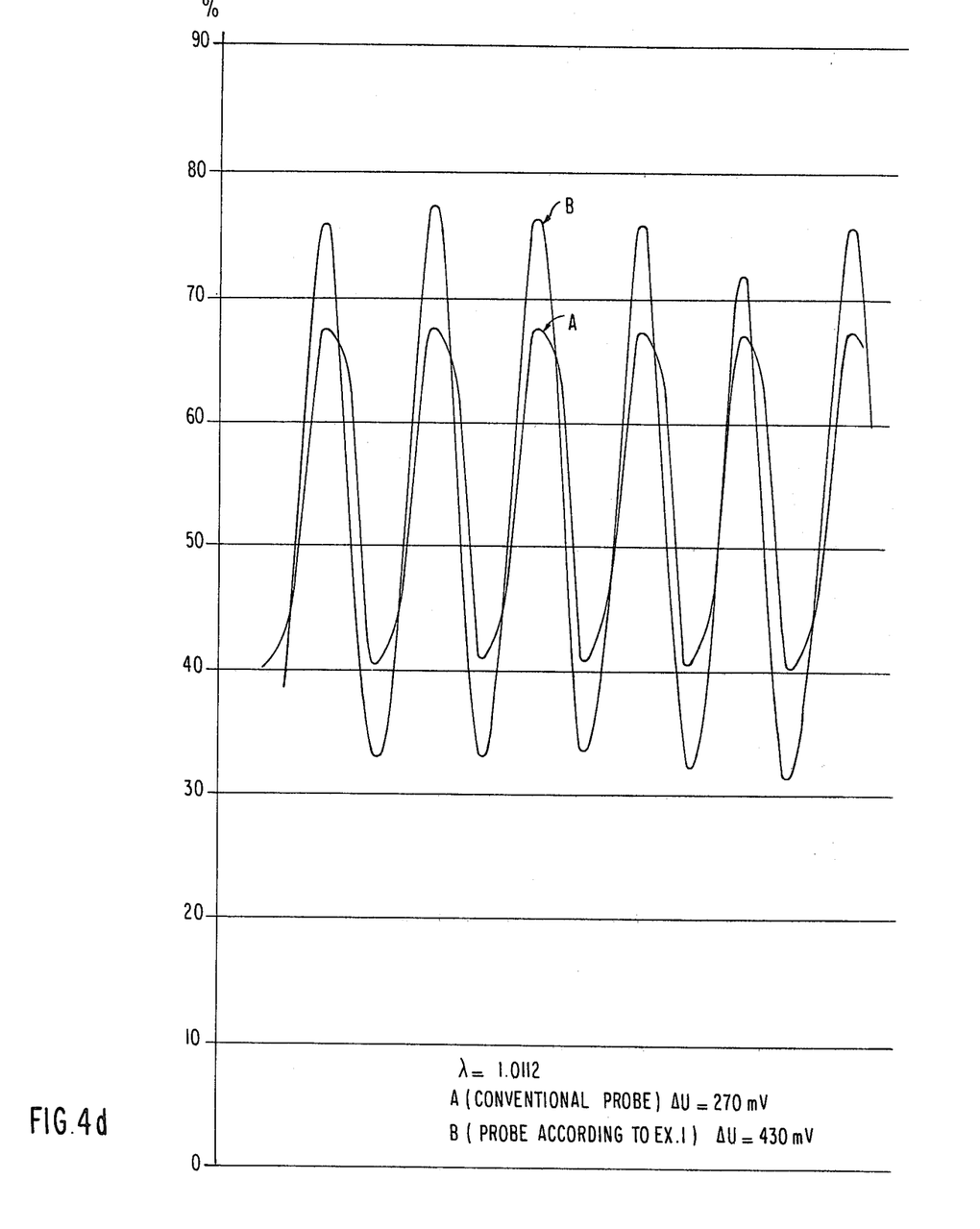
Figure 4E:
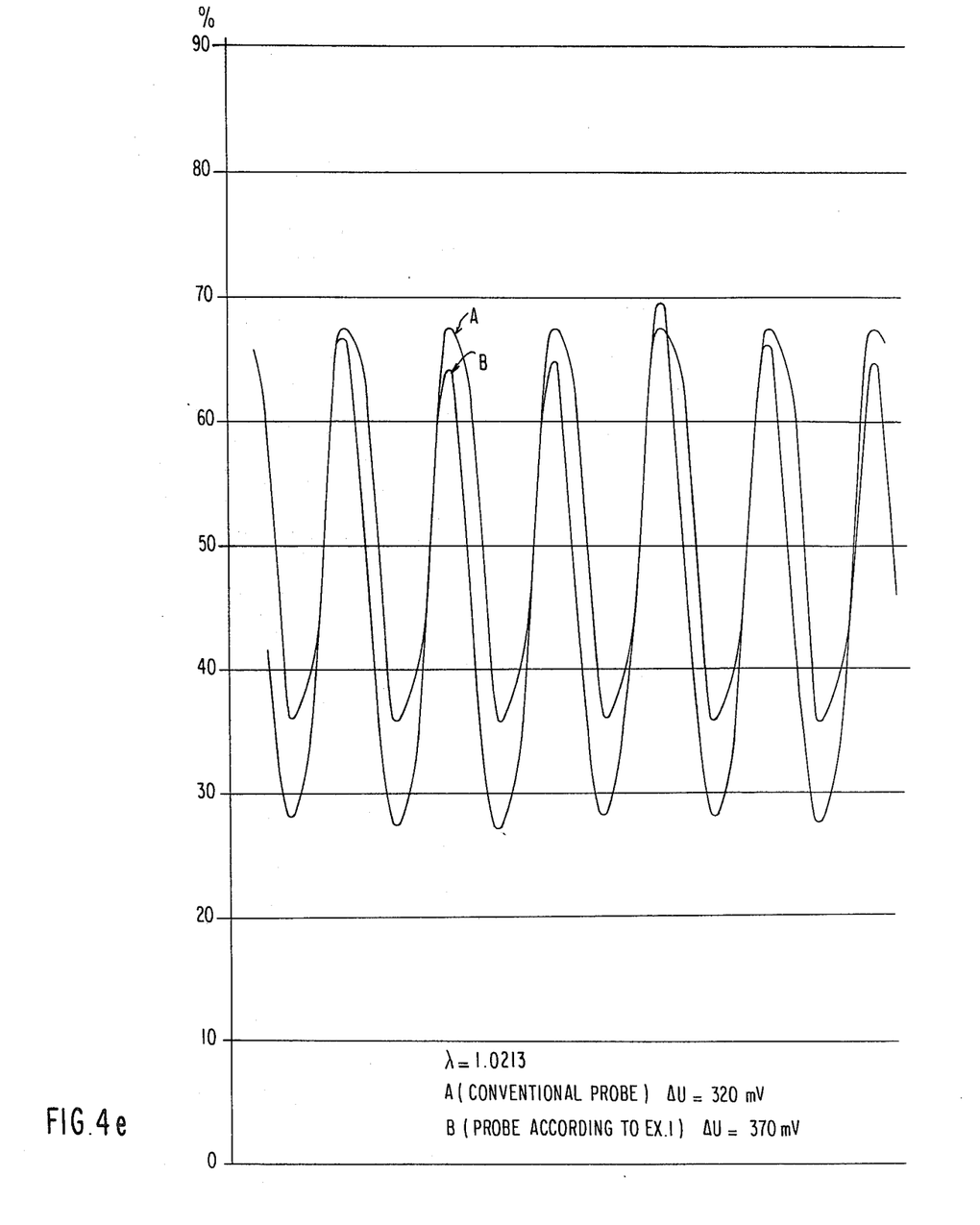
Figure 5A:
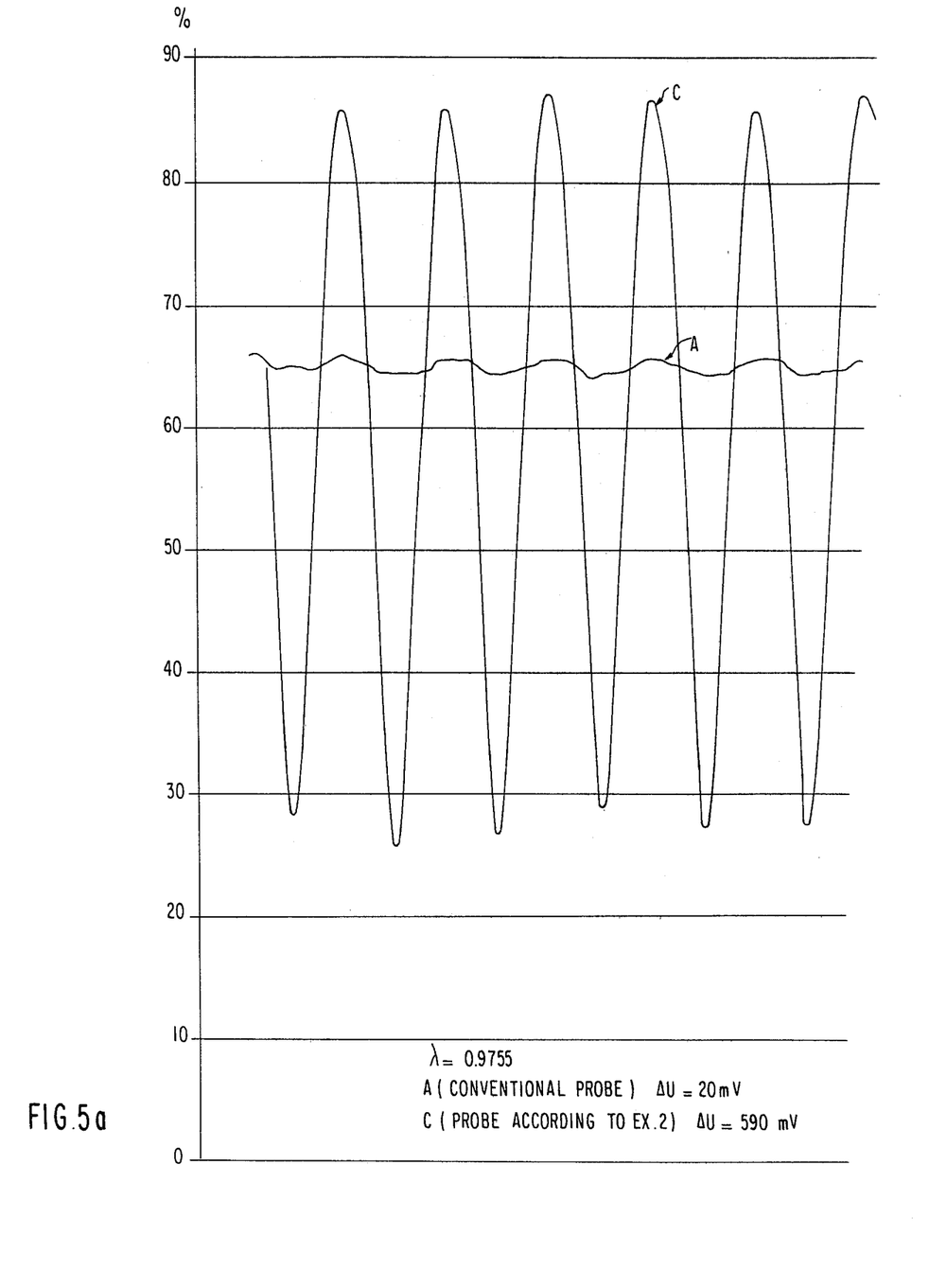
FIGS. 5a–5e are graphs showing sensor signals of a commercial oxygen sensor and of an oxygen sensor according to the invention in the case of air/fuel ratios of $\lambda = 0.9755–1.0231$, wherein the platinum group metal component was applied onto an intermediate layer of active aluminum oxide applied additionally onto the wire gauze, and functioning as a carrier for the catalytically active noble metals.
Figure 5B:
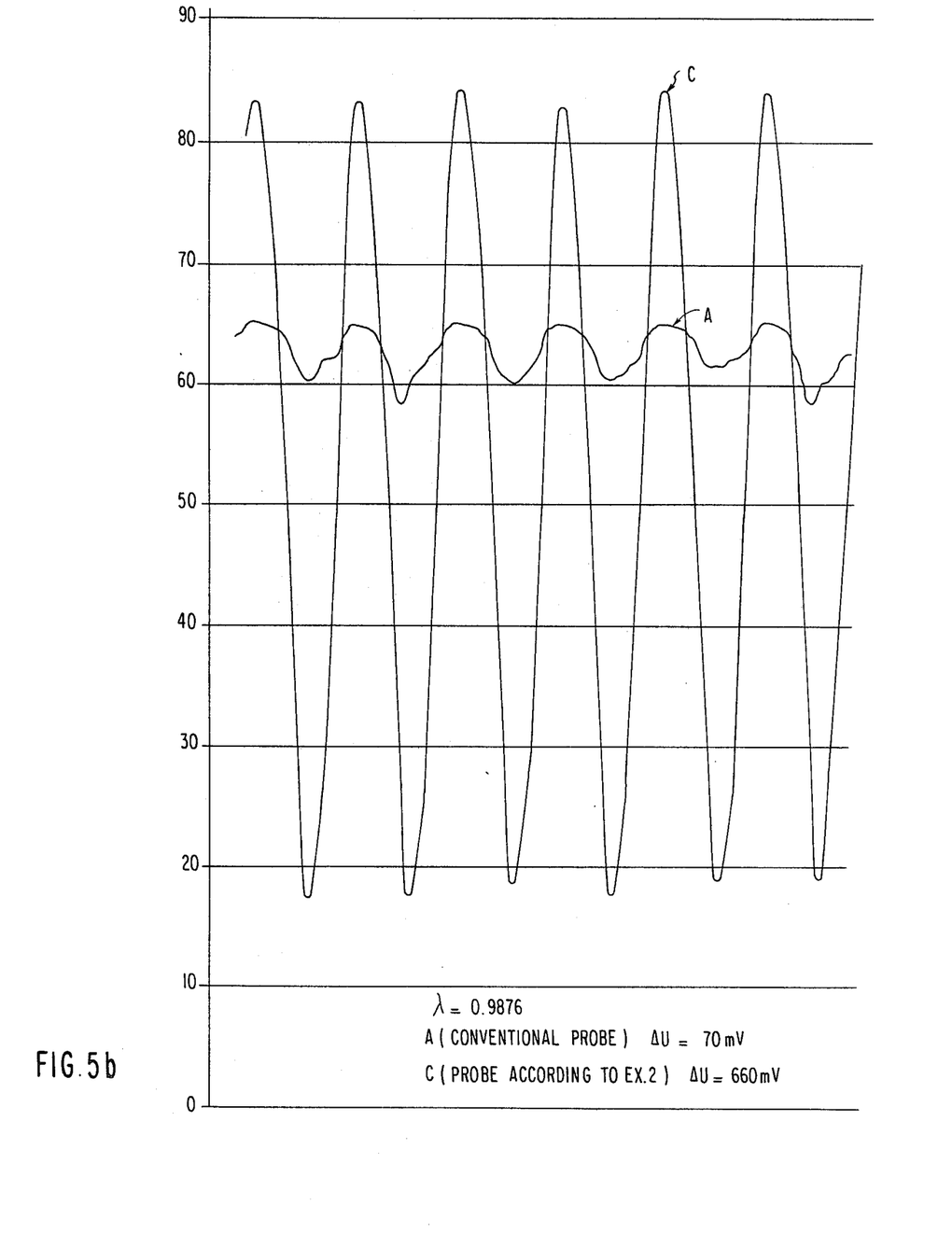
Figure 5C:
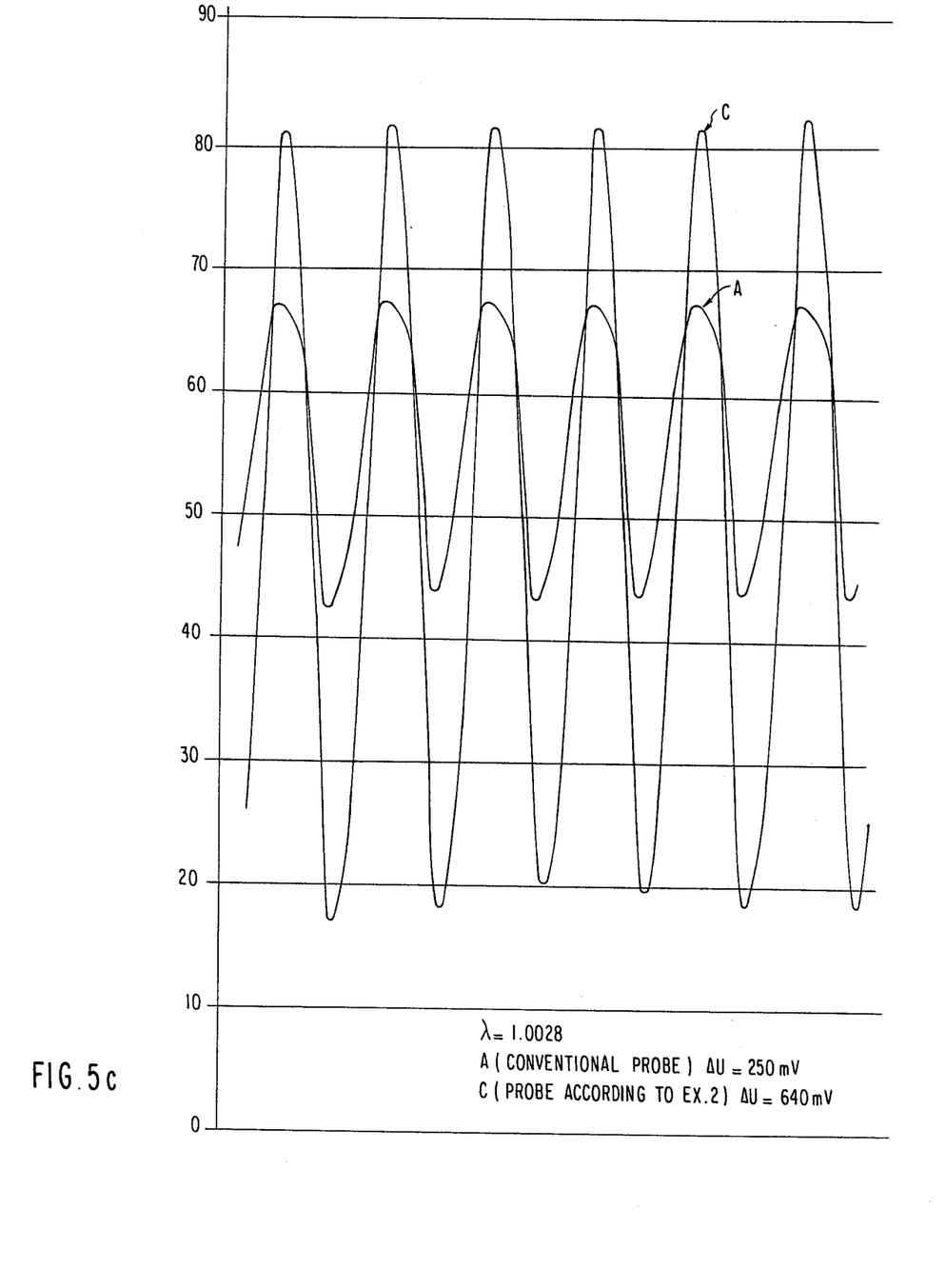
Figure 5D:
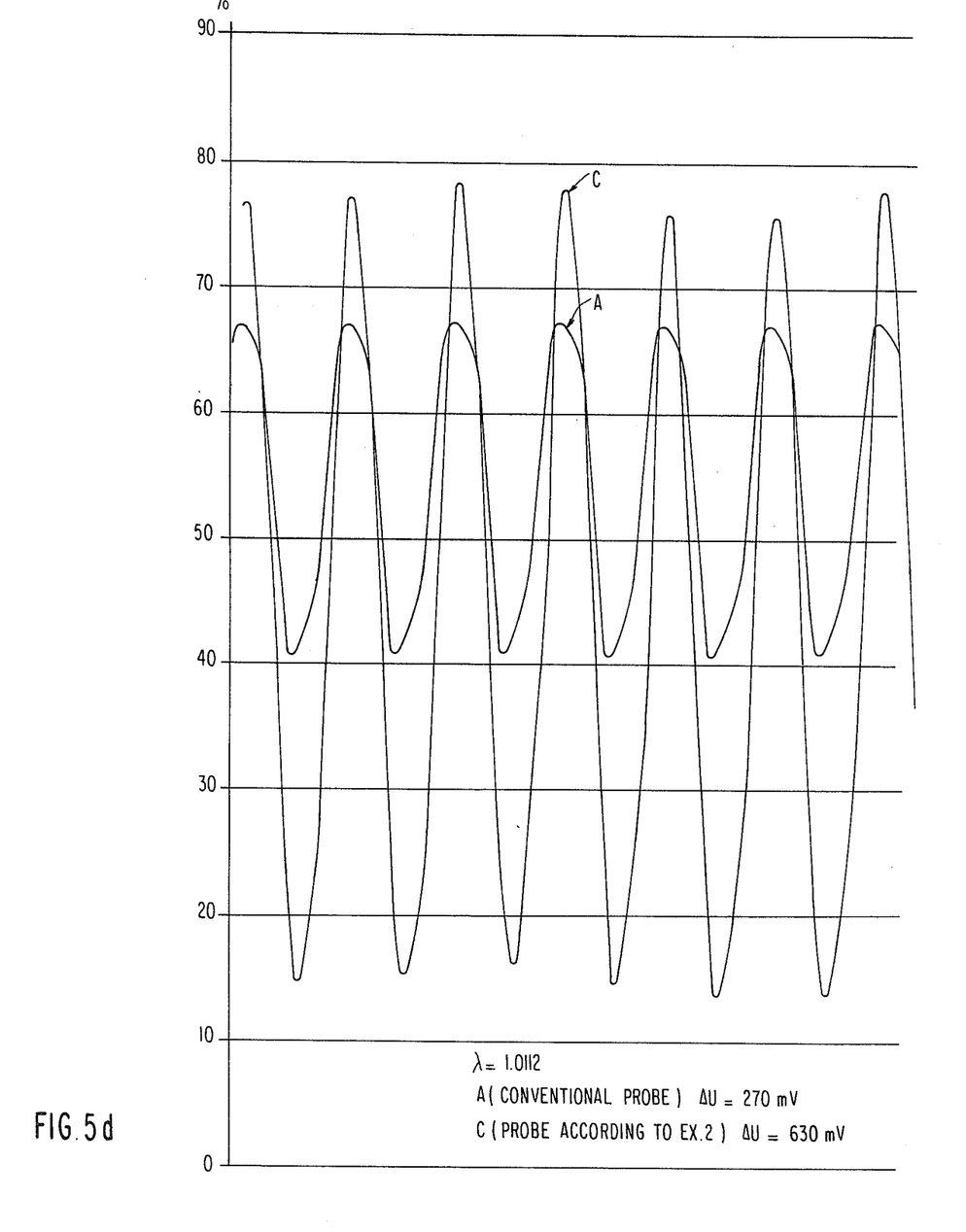
Figure 5E:
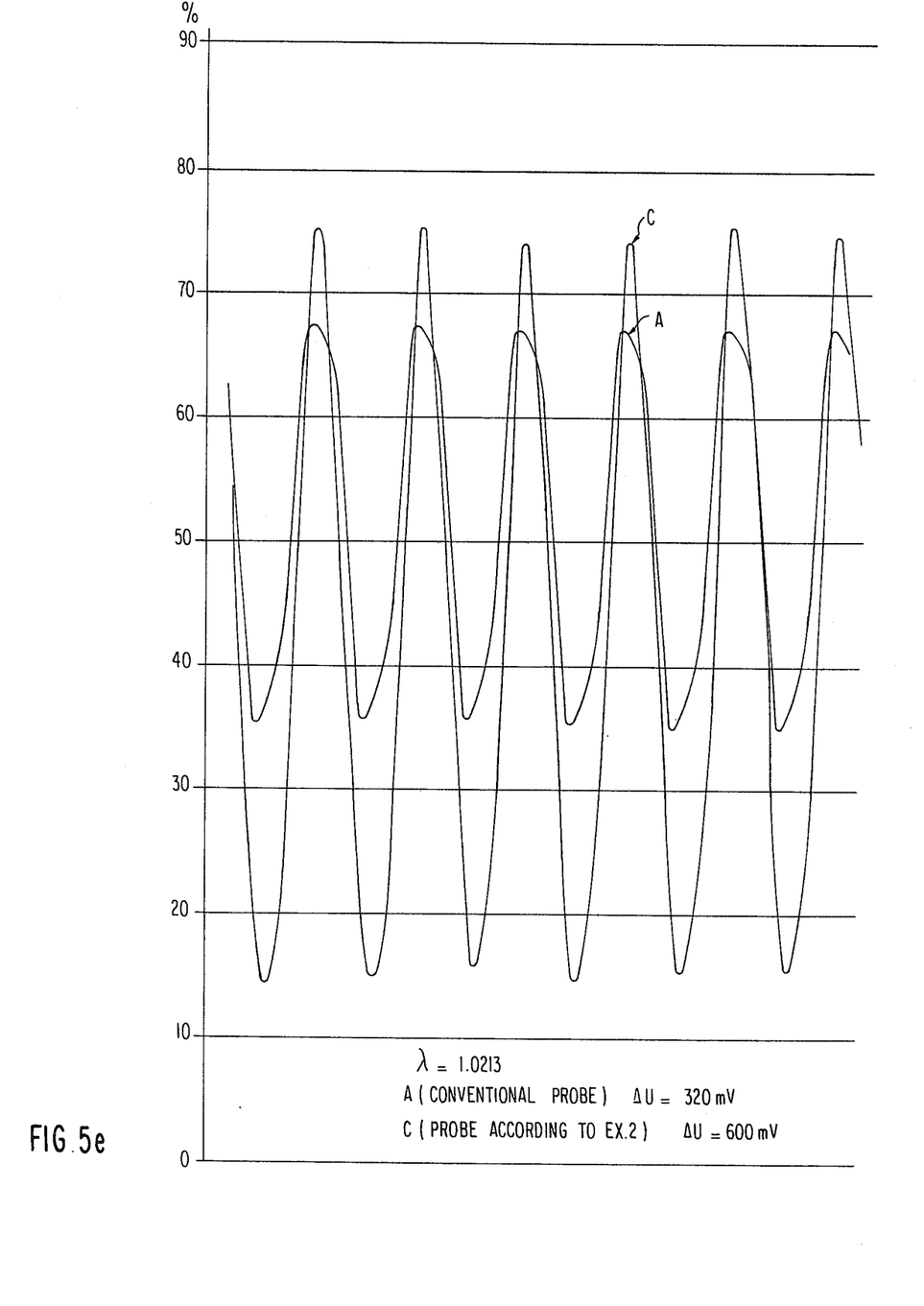

FIG. 2 is a schematic diagram showing the arrangement used for testing the $\lambda$-sensor according to the invention from the point of view of application technology. In this arrangement, position 9 represents the engine and the control unit 10 controls, the preparation of the combustion mixture. The action of the control unit 10 is influenced by the oxygen sensor 11, which is arranged in the stream of exhaust gas of the engine. The stream of exhaust gas is guided past the $\lambda$-sensors 12 and 13, wherein the sensor 13 represents an embodiment improved in accordance with the invention. FIG. 2A shows details of the sensors. Oxygen of the air is fed periodically (1Hz) to the exhaust gas with the help of the time relay 14, as a result of which the $\lambda$-value oscillates with $\pm \lambda = 0.07$ around a predetermined mixture ratio. The recorder 15 records signals of the two different sensors 12 and 13. A part of the exhaust gas stream is fed to the analyzing equipment 16 in order to continuously control the composition of the exhaust gas. The results are recorded on the recorder 17.

EXAMPLE 1

A wire gauze with a mesh width of 0.1 mm and a wire diameter of 0.07 mm of working material No. 1,4725 (registered trademark Aluchrom W; 15% Cr, 5% Al, Ce, rest iron) is annealed for 3 hours at 900° C. in an atmosphere containing oxygen. The wire mesh treated in this way is attached in three layers to a commercial sensor as shown in FIG. 1. After preheating of the jacket to 70° C., the impregnation with a noble metal takes place by application of an alcoholic solution (methanol) of $H_2PtCl_6$ and $RhCl_3$, which are present in the solution with a metal ratio of Pt/Rh=5:1. The entire quantity of noble metal applied to the screen cloth amounts to 50 mg per sensor. Following the impregnation, the sensor is dried lightly.

EXAMPLE 2

A wire gauze as in Example 1 is used and is subjected to the same pretreatment for 3 hours at 900° C. After attaching three layers in the sequence shown in FIG. 1, 0.1 g of active $Al_2O_3$ per sensor are applied to the wire gauze. Subsequently, annealing at 500° C. for 2 hours results in an aluminum oxide with a specific surface of 120 m$^2$/g. The impregnation of the catalysis promoting intermediate layer is accomplished in the same manner and with the same noble metal ratio or noble metal covering as in Example 1.

EXAMPLE 3

A commercial oxygen measuring sensor and a sensor improved according to the invention and produced according to Example 1 are built into an arrangement shown in FIG. 2 for application technology testing. In the case of the same load point and the same exhaust gas temperature, the mean λ-value of the air/fuel mixture is changed gradually from the rich toward the lean side. By a pulsating addition of air, (frequency 1 Hz), the λ-value at the same time fluctuates periodically by ±0.07. This method of operation corresponds approximately to the operation of the vehicle with a controlled adjustment of the mixture. The signals of the two sensors are recorded by the recorder 15 in FIG. 2 and are shown in FIGS. 4a-4e; the evaluated data are contained in Table 1.

TABLE 1

Height of the sensor signal in mV of a commercial sensor (A) and a sensor (B) improved according to Example 1.

| λ | Sensor A | Sensor B |
| --- | --- | --- |
| 0.9755 | 20 | 310 |
| 0.9871 | 80 | 390 |
| 1.0028 | 250 | 450 |
| 1.0112 | 270 | 430 |
| 1.0213 | 320 | 370 |

As may be readily seen from FIG. 4 (a-e), the sensor improved in accordance with the invention has clear advantages as compared to commercial measuring sensors. In the case of air/fuel ratios of λ≦1, the signal of the sensor (A) is developed only imperfectly and not well defined and is therefore poorly suited to act on the controller to influence the combustion mixture. This leads to irregularities in the formation of the fuel mixture and thus to an increased consumption of fuel and to a higher emission of pollutants. The sensor (B) improved according to the invention on the contrary, has a uniform, well-shaped sensor signal over the entire λ-range covered, which permits a considerably more precise control of the fuel mixture formation to achieve the optimum operating point of a three-way catalyst. Saving of fuel and above all a considerable improvement of the emission values, especially of the nitric oxide emission, are achieved.

EXAMPLE 4

As in Example 3, a commercial oxygen sensor and one improved according to the invention were produced according to Example 2 and inserted into the arrangement shown in FIG. 2 in order to conduct application tecnology tests. The testing was accomplished in the same way as in Example 3. The sensor signals obtained are given in FIG. 5a-5e and the data evaluated are set forth in Table 2

TABLE 2

Height of the sensor signal in mV of a commercial sensor (A) and a sensor (C) improved according to Example 2

| λ | Sensor A | Sensor B |
| --- | --- | --- |
| 0.9755 | 20 | 590 |
| 0.9876 | 70 | 660 |
| 1.0028 | 250 | 640 |
| 1.0112 | 270 | 630 |
| 1.0213 | 320 | 600 |

Here again in the base of the sensor (C) according to the invention, there results a clear advantage as compared to a commercially obtained oxygen sensor. In this case however, the differences are still more marked than in the case of Example 3, and the height of the signals of the sensor (C) may be considered as linear over the entire λ-area covered, and thus act as an excellent actuating variable for the optimum control of systems as needed for the formation of the combustion mixture of an intenal combustion engine.

We claim:

1. In a sensor for the measurement of the oxygen content in the exhaust gas of internal combustion engines, wherein the solid substance electrolyte sensor element which serves as a producer of electrical sensor signals is fitted with a catalytically active gas permeable wrapping spaced apart from and not in contact with said sensor element, the improvement wherein the wrapping consists of at least one layer of wire gauze of an alloy containing iron, chromium and aluminum surrounding a perforated protection tube surrounding said sensor element, said wire gauze being coated with an intermediate layer of metal oxide promoting catalysis and said intermediate layer being impregnated with a metal of the platinum group or with a combination of at least one platinum group metal and at least one base metal.

2. The sensor as in claim 1 wherein a catalyst material is precipitated directly on the wire gauze wrapping.

3. The sensor as in claim 1 wherein an intermediate layer is present consisting of an aluminum oxide of the transition series which promotes catalysis.

4. The sensor as in claim 1, wherein a platinum/rhodium composition is used as the catalyst promoting material.

5. The sensor as in claim 1 wherein a platinum/rhoduium/aluminum composition is used as the catalyst promoting material.

6. A method for the production of a voltage corresponding to the residual oxygen concentration in the exhaust gases of internal combustion engines as a value for adjustment of the composition of the air/fuel ratio, comprising inserting into the exhaust line of an internal combustion engine, the probe as defined in claim 1, and thereby causing a voltage to be generated which imparts a signal to the controller of the fuel/air mixture for control thereof.

* * * * *